US00PP09361P

United States Patent [19]

Smith

[11] Patent Number: Plant 9,361

[45] Date of Patent: Nov. 7, 1995

[54] 'GEORGE'S RED' PEACH TREE

[76] Inventor: George F. Smith, 37476 Colorado Rd., Avon, Ohio 44011

[21] Appl. No.: 123,795

[22] Filed: Sep. 20, 1993

[51] Int. Cl.[6] ..... A01H 5/00

[52] U.S. Cl. ..... Plt./43.2

[58] Field of Search ..... Plt./43.2

[56] References Cited

U.S. PATENT DOCUMENTS

P.P. 8,211 4/1993 Janzen ..... Plt./42.3

*Primary Examiner*—James R. Feyrer

[57] ABSTRACT

A new peach tree of standard size, which yields heavy crops of large fruit in about the last week of July to the first week of August in Avon, Ohio. The tree is spreading in habit and of normal density. Fruit has an attractively patterned over-color a golden ground color; fruit is large, freestone, of rounded, attractive shape, and has firm, juicy yellow flesh with some red flecking. The tree, being self-fertile, may be planted alone in a home garden without having to plant a pollinator tree within pollination distance.

1 Drawing Sheet

BACKGROUND OF THE TREE

The present discovery relates to a new and distinct peach tree, *Prunus persica,* which has been denominated as the variety 'George's Red'. The tree of this invention is of standard size and normal appearance, and yields large fruit with yellow flesh, skin having a yellow to golden ground color and a heavy red over-color which is expressed in blushes and mottling and broad blotches over the blushed ground color. The stone is free rather than cling, and is smaller than normal for the size of the fruit; with the flesh having only a tinge or minute amount of red flecking and striations, and only a scant amount of red coloration on the surface of the pit well. Fruit of this variety is mature for harvesting about July 28 to about August 6, and has an attractive appearance due to a light pubescence and bright red over-color which pleasingly contrasts with a bright golden-yellow ground color.

DISCOVERY OF THE TREE

The tree of this invention was a chance seedling which appeared with about nine other seedlings in the garlic and parsley bed portion of my home garden. The source of the seedlings is unknown, but they are believed to have developed from pits which were deposited from fruit which had been eaten, and from seeds which had been planted by me at distances of about two to three feet apart. Among the germinated seedlings, the seedling of this invention was immediately conspicuous when compared to the other sprouted seedlings because it was larger and more vigorous than the remaining tree seedlings. Based on the vigor and healthy appearance of this tree, it was allowed to remain, while the nine other seedlings were removed. The selected tree was allowed to grow to maturity where it was discovered, with the hope that it would develop into a healthy tree which would produce fruit for home use. The tree was soon discovered to be precocious when it bloomed and fruited after a mere three years of growth, and was noted to produce large, freestone fruit of exceptional quality, size, appearance and taste. After several years of observation, after blooming and fruiting, it was discovered that this tree was also exceptional in the size, quality, timing and production of its fruit, and by its growth into a tree of at least normal size and strength. With the discovery of these outstanding attributes, it was believed that this would be an excellent tree for introduction into industry as a commercial variety.

ASEXUAL REPRODUCTION OF THE TREE

The tree of this invention has been asexually reproduced by my direction by budding by the personnel of and at the facilities of Newark Nurseries, Inc., at 60397 CR 681, Hartford, Mich. Clonal specimens of this tree have been planted for observation and testing at this facility, as well as in my home garden in Avon, Ohio. Due to the half-hardy nature of this tree, the original specimen was lost due to the killing nature of the cold weather of the very severe winter of 1993–1994. To date, the clonal specimens of this tree have been observed to faithfully express the distinguishing characteristics and be identical to the original parent tree in these characteristics, establishing that the tree is genetically stable.

BRIEF DESCRIPTION OF THE VIEWS OF THE DRAWING

In the accompanying drawing, the tree of this discovery is depicted in the photographs, one above the other, which show:

In the top photograph, at the top portion of the photograph, a single fruit is depicted as it has been split apart at the plane of the suture to reveal the flesh color, pit well on the left half of the specimen, and the stone retained within the half of the fruit on the right side of the photograph. A row of fruit is shown in the middle portion of the photograph, with three separate specimens depicted. On the left is a fruit so positioned as to depict the stem end of the fruit. In the middle is a second specimen which shows the shape and color patterning seen in the fruit of this tree in side view. On the right is a third specimen of the fruit oriented to show the blossom end of the fruit, the rounded shape of the fruit and the suture line. At the bottom of the top photograph there is a standard sized golf ball pictured for comparison of scale.

The bottom photograph depicts the original specimen of the tree of this invention during the harvest season, the shape of the tree, the branching and foliar density of the tree, and the extent and strength of the canopy. A portion of the fruit crop has been retained on the tree to show the size, coloration of the crop borne by the tree, and the ability of the tree to support a heavy crop of fruit.

DETAILED BOTANICAL DESCRIPTION OF THE TREE

The descriptions of the pomological characteristics of the tree which are presented below were taken from the oldest specimen of the tree before it was killed, and from clonal progeny resulting from the tree, as cultured in my private orchard area and garden near Avon, Ohio. While the characteristics presented are viewed to accurately, botanically describe the tree, the phenotypical characteristics and morphology of the tree would be expected to slightly vary by the skilled artisan as a function of growing location and cultural conditions. The tree depicted has not been severely pruned or trained to any specific growing system. Color values presented are defined from reference to the *Royal Horticultural Society Colour Chart,* Royal Horticultural Society, London England, where coloration may be helpful in distinguishing the tree of this application. Where not critical and descriptive, coloration is defined in ordinary terms of common meaning.

Tree:

*Botanical classification.—Prunus persica.*

*Commercial classification.*—Mid-season, freestone, yellow fleshed peach.

*Parentage.*—Unknown, seedling in my home garden in Avon, Ohio.

Habit:

*Size.*—Normal, full-sized tree.

*Habit.*—Normal, more spreading than ascending; the oldest specimen attained a height of 8 feet and a width of 9 feet in the space of five years to the time of the observation.

*Vigor.*—Moderate or average. A young but mature specimen of the tree commonly attains from about 8 to about 19 inches of terminal growth in a typical year at Avon, Ohio.

*Shape or figure.*—Broad, spreading and fairly open. Normally slightly broader than tall. Determined by pruning and training.

*Trunk.*—Slim to moderably thick, but strong.

*Branching habit.*—Strong. The branching does not substantially differ from that of the species. This tree may be trained to an open center with several well spaced, strong lateral or scaffold branches. The natural angle of scaffold branches is about 40 to 60 degrees from the axis of the trunk of the tree, and is of sufficient strength to support a heavy crop without supplemental support, as shown in the bottom photograph of the drawing.

*Canopy density.*—Moderately but not overly dense. This tree requires little detail pruning to attain a tree of sufficient strength and form and canopy density for development of an optimum number of and placement of fruit, with minimal requirements for thinning.

*Density of foliage.*—Moderately dense. The internode length of this tree ranges from between near ¼ inch to about 1 inch, depending on the seasonal timing of growth. Foliar density is about optimum and average for commercial sized peach trees, allowing for good light exposure of most of the fruit formed, and results in a high level of red coloration of most of the fruit.

*Productivity.*—Productive.

*Tenderness.*—Half-hardy. About average in susceptibility to winter cold damage to flower buds. Susceptible to winter killing temperatures.

*Regularity of bearing.*—Under normal circumstances, the tree is a regular bearer.

Bark:

*Mature color.*—The bark of mature wood is reddish-brown, with a slight overcast of grey, near RHS Greyed-Orange Group 166B, and with more grey with increasing age.

*Mature textile.*—Fairly smooth, with some slight vertical furrowing.

*Mature lenticels.*—Essentially horizontal lines ranging between about ⅛ inch to about ¼ in length, and about 1/16 inch in width. Corky in color and appearance.

*New, character and color.*—The bark of the twigs is initially green but turns progressively more tan-red, as the season progresses, to near RHS 166C. Lenticels on twigs are fairly typical of the species in density, color and size.

Buds:

*Size.*—Between about ¼ to ⅝ in width.

*Character.*—Plump, acuminate with acute point. Not dissimilar from those of the species.

Foliage:

*Form.*—Normal, linear lanceolate. Slightly arching along the midrib bottom, rendering leaves reflexed to a moderate degree.

*Margin.*—Normal, crenated.

*Length.*—About 6½ inches, or longer.

*Width.*—Ranging from about ¾ inch to about 1 7/16 inches.

*Leaf stem length.*—Long, to about 1¾ inches.

*Leaf stem thickness.*—Normal.

*Color.*—Top surface near RHS 139B. Bottom surface near RHS 138B.

*Glands.*—Normally 2 in number, but 3 or 4 may be seen at the base of the leaf blade, or glands may be absent in some leaves. Color is light green in spring, darkening in summer. Gland shape is generally round.

*Stipules.*—Long, narrow and serrated at the base of the petiole; early deciduous.

Blooming:

*Dates.*—Not recorded, but believed to be substantially mid-season.

*Flower buds.*—Shape and the size of the flower buds are about normal of the species, although the characteristics of the flower buds have not be systematically recorded.

*Flowers.*—Showy, about ¾ inch in size, to larger. Flowers are regarded as typical for the species and as being unique only in the production of self-fertile pollen.

*Petal color.*—Pink fading to near white.

*Self-fertility.*—This tree has been established to be self-fertile due to its ample production of large fruit crops in an isolated location.

Fruit:

*Maturity when described.*—Ripe for commercial harvest, shipping and eating, Jul. 28 through Aug. 6, 1993. Ripens approximately two weeks prior to the variety 'Red Haven' in the same area of production.

*Size.*—Generally large and uniform. Length on axis is about 3¼ inches; length along the suture is about 2⅝ to 2¾ inches, or longer. Width of the fruit is between about 3 to 3¼ inches. Weigh ½ pound or more.

*Symmetry.*—Slightly lobed on one side of the suture to near symmetrical.

*Suture.*—Distinct to indistinct, slightly indented and very slightly lipped, moderately inconspicuous. Skin color in the suture is indistinct from the color along the sides of the suture. Slight depression beyond the pistil point.

*Pistil point.*—Smoothly nubbed to absent. Does not normally protrude beyond the rise of the apical portion of the fruit.

*Ventral surface.*—Gently rounded.

*Stem cavity.*—Slightly to moderately shallow, oval. Moderately to severely abruptly shouldered. Shoulders may show branch indentation from carriage on tree. Depth of the stem cavity is ¼ inch, or more and width is about 5/16.

*Stem length.*—About ½ inch.

*Stem diameter.*—Normal, strong.

*Shape.*—General observations — The fruit is generally uniform in shape and appearance, and highly attractive from the standpoint of being smooth and rounded. The pistil point is abbreviated or absent which could be advantageous in prevention of bruising and entry of rot causing microorganisms into the flesh of the fruit in shipping and storage.

*Skin thickness.*—Medium, tenacious to the flesh.

*Ground color.*—Golden orange at ripeness, near RHS 23B.

*Skin overcolor.*—Darker zones of high exposure usually color to shades between Greyed–Red Group RHS 178B to RHS 180A, with the overcolor covering about 80% or more of the skin surface. Most of the overcolor is a bright and attractive shade between about RHS 34A, and RHS 42B, but the shades of the overcolor vary with the exposure offered by the location of the fruit on the tree.

*Skin color patterns.*—The overcolor may be blushed on most fruit but may also occur as blotches of irregular darker strips over a fainter overcolor blush. Blotches of such a pattern may be less conspicuous if the fruit is highly exposed and of advanced ripeness at picking. Most fruit has attractive shading from dark to lighter areas of overcolor density, and few, small unblushed areas of contrasting shades of orange, gold and yellow tones of ground color.

*Skin hair.*—Tomentum is fine to very fine and scant. Hairs can be seen only as a light, white shading on the surface of the skin.

*Flesh color.*—Fairly deep yellow, near Yellow-Orange Group 20A. There are slight striations of red within the flesh of the fruit which are of no distinct pattern but appear predominantly on the same side of the fruit as the keel of the stone.

*Flesh character.*—Firm, even when eating ripe. Ripens uniformly.

*Taste.*—Sweet, with classic peach flavor.

*Juice.*—Ample, very sweet.

*Pit well.*—Does not extend beyond stone and conforms intimately to the surface of the stone. Color is substantially the same as that of the flesh or slightly lighter.

*Length.*—About 1 9/16 inches, but may vary by about 1/32 inch.

*Width.*—1⅛ inch, with about the 1/32 inch possible variance.

*Thickness.*—Near ¾ inch, with about a 1/32 inch variation.

*Form.*—Substantially oval.

*Apex.*—Blumted.

*Color.*—Brown, near Greyed Orange Group RHS 176A.

*Base.*—Tapered, and normal to the axis of the stone.

*Sides.*—Equal and furrowed throughout, with occasional pits.

*Hilum.*—Distinctly present but normal in character.

*Ventral edge.*—Keel-shaped, of uniform extend along stone's edge.

*Dorsal edge.*—Generally smooth, curved.

*Tendency of stone to split.*—The stone has not been seen to split.

Keeping quality and use: The fruit of this tree is of attractive size, shape and appearance which makes it of the highest quality for local markets when picked ripe, due to the pleasant taste and high level of juice. The firmness of the flesh and advantageous smooth surface of the fruit of this peach tree is anticipated to allow fruit to withstand shipping and handling to as high a degree as the best of the current market available peaches of the same season.

I claim:

1. A new and distinct variety of peach tree substantially as illustrated and described.

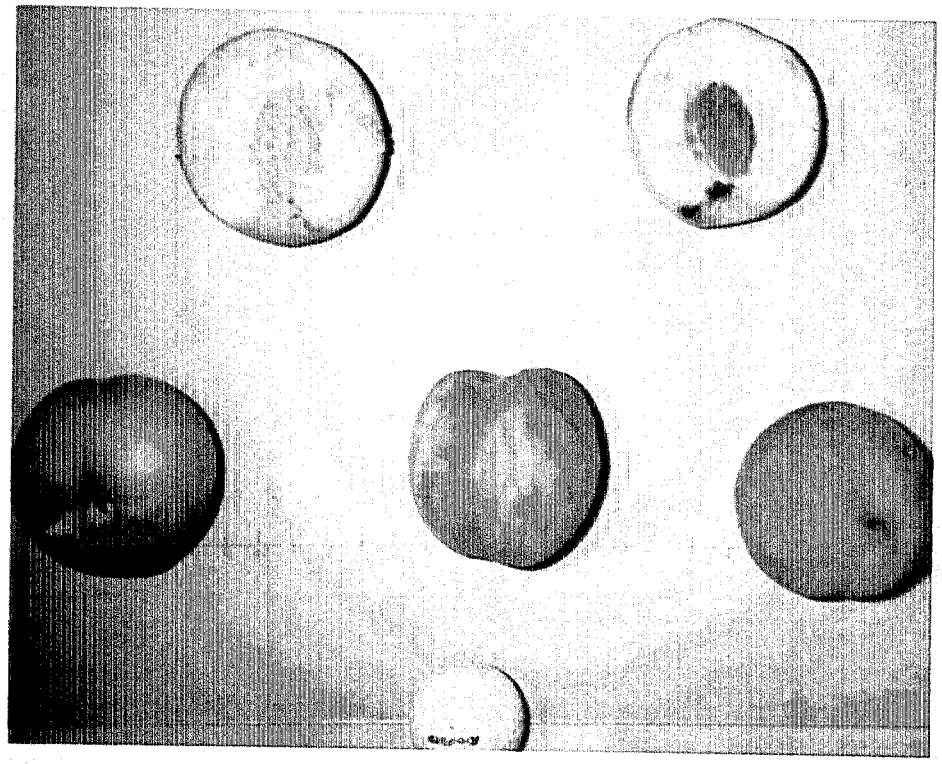
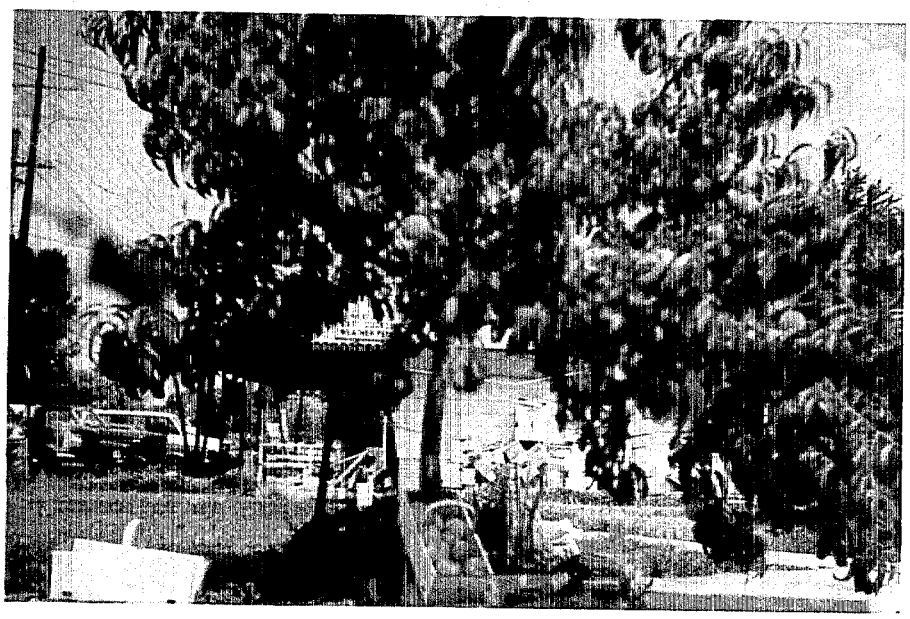

* * * * *